United States Patent [19]
Kanas

[11] Patent Number: 5,232,362
[45] Date of Patent: Aug. 3, 1993

[54] DENTAL SUCTION APPLIANCE

[76] Inventor: David C. Kanas, 11279 Serpentine Ct., Gold River, Calif. 95670

[21] Appl. No.: 959,035

[22] Filed: Oct. 8, 1992

[51] Int. Cl.5 .................. A61C 17/06; A61C 17/14
[52] U.S. Cl. ........................................ 433/93; 433/91
[58] Field of Search .................... 433/91, 93, 94, 126, 433/116

[56] References Cited

U.S. PATENT DOCUMENTS

| 594,952 | 12/1897 | Hoyer . |  |
|---|---|---|---|
| 1,004,118 | 9/1911 | Waters . |  |
| 1,067,571 | 7/1913 | Abbott . |  |
| 1,152,122 | 8/1915 | Samphere . |  |
| 1,516,933 | 2/1924 | Terronova . |  |
| 2,671,269 | 3/1954 | Francis . |  |
| 2,731,722 | 8/1954 | Wilen . |  |
| 2,924,013 | 1/1959 | Wowra . |  |
| 3,090,122 | 5/1963 | Erickson | 433/93 |
| 3,512,258 | 5/1970 | Johnson | 433/91 |
| 3,777,756 | 12/1973 | Lohr | 433/91 |
| 3,924,333 | 12/1975 | Erickson . |  |
| 4,024,642 | 5/1977 | Zorovich | 433/93 |
| 4,701,128 | 10/1987 | Fitzig et al. . |  |
| 4,975,057 | 12/1990 | Dyfvermark | 433/93 |

OTHER PUBLICATIONS

Advertisement by Future Dentistry Inc. for Aspirating Device published in Dental Products Report Nov. 1992.

Primary Examiner—Gene Mancene
Assistant Examiner—Cindy A. Cherichetti
Attorney, Agent, or Firm—John P. O'Banion

[57] ABSTRACT

An apparatus (10) for use during dental procedures is disclosed. A tongue deflector (12) is coupled to an aspiration tube (24). The aspiration tube (24) is in turn coupled to a bite tube (38) which is held in place by a patient's teeth. A vacuum gap (30) provides suction sufficient to aspirate liquid and small particles of debris which collect during a dental procedure, while bite tube (38) maintains the patient's mouth in an open position and tongue deflector (12) retracts the patient's tongue away from the area in which the dental procedure is being performed. By sliding aspiration tube (24) in relation to tongue deflector (12), the level of suction can be controlled.

19 Claims, 4 Drawing Sheets

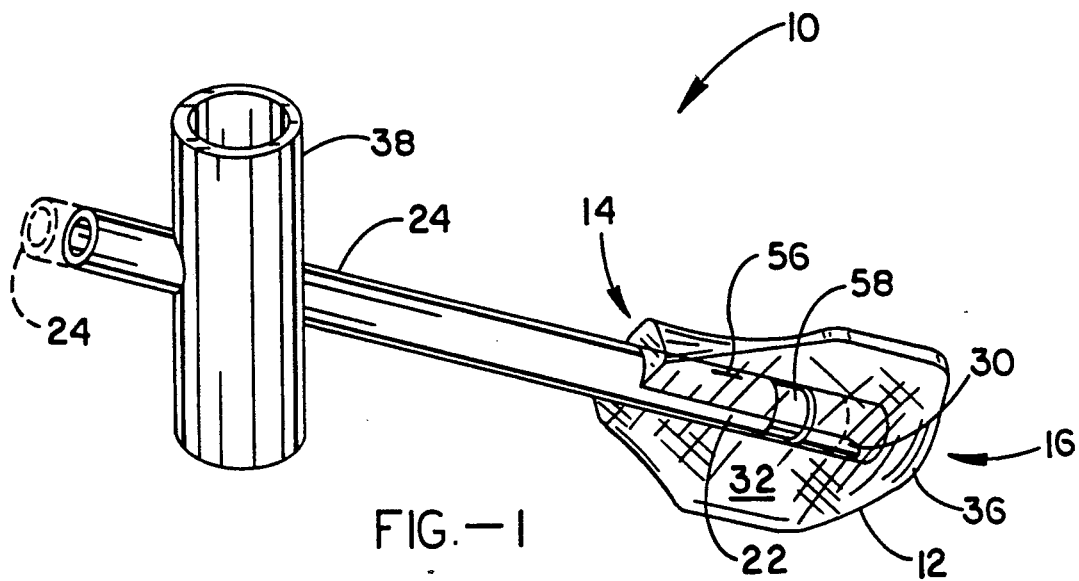
FIG.—1
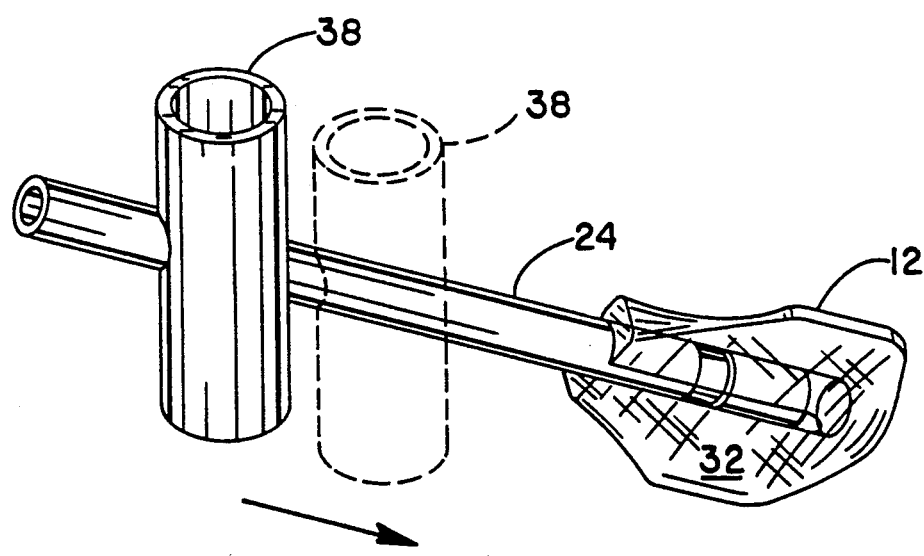
FIG.—8

DENTAL SUCTION APPLIANCE

BACKGROUND OF THE INVENTION

1. Field of the Invention

This invention pertains generally to dental appliances, and more particularly to an apparatus for deflecting the tongue, aspirating liquids, and maintaining the patient's mouth in an open position during oral surgery and other dental procedures.

2. Description of the Background Art

A common problem for dentists and dental hygienists performing surgery and other dental procedures is the removal of saliva generated by the patient, removal of water used to cool high speed drills, and removal of water and other liquids used in connection with certain procedures. During most of these procedures, the dentist, dental assistant, or hygienist must manually place a suction tube in the patient's mouth for aspiration of liquids. And, in order to achieve proper and efficient aspiration, it is often necessary to hold the suction tube in place or to move it around in a vacuuming motion.

In addition, it is often necessary for the dentist or dental assistant to deflect the patient's tongue away from the area in which work is being performed. And, during the time that the procedure is being performed, the patient undergoes stress in an effort to keep his or her mouth in an open position.

As a result, the work space inside the mouth is reduced or otherwise encumbered by the various dental appliances being used by the dentist and the dental assistant. In addition, the patient's jaw muscles become tense and it be difficult for the patient to maintain the mouth in an open position.

Various devices have been developed to assist the dentist while performing dental procedures. For example, U.S. Pat. No. 4,975,057 issued to Dyfvermark on Dec. 4, 1990, discloses a bite block having an aperture for insertion of a suction nozzle associated with an aspiration device. However, this particular device is not suited for use by patients who are missing teeth and cannot effectively clamp the bite block in place and, furthermore, does not provide for deflecting the tongue away from the work area. U.S. Pat. No. 4,024,642 issued to Zorovich on May 24, 1977, discloses a bite block coupled to an hour-glass shaped shield having a system of suction channels. This device, however, does not deflect the tongue, greatly restricts the dentist's work area, and requires external control of the level of suction. U.S. Pat. No. 3,924,333 issued to Erickson on Dec. 9, 1975, discloses a bite block with left and right tongue guards and a series of channels which communicate with an evacuation tube. This device, however, cannot be held in place where a patient has several missing teeth, cannot be easily installed and removed in the mouth, and is difficult to use. U.S. Pat. No. 3,090,122 issued to Erickson on May 21, 1963, discloses a receptacle for placement in one side of the mouth, and has apertures and drains for aspirating fluids. This device, however, is best suited for a reclining patient and severely limits the dentist's work space.

Thus described have been devices which are independent of the handpiece used by the dentist. However, various tongue deflectors and shields can be found as attachments for a handpiece. For example, U.S. Pat. No. 1,004,118 issued to Waters on Sep. 26, 1911, discloses a handpiece mounted shield having slotted receptacles to allow the position of the shield to be changed for working on either side of the mouth. U.S. Pat. No. 1,067,571 issued to Abbott on Jul. 15, 1913, discloses a handpiece mounted shield which can be rotated from side to side. U.S. Pat. No. 2,671,269 issued to Francis on Mar. 9, 1954, discloses a tongue deflector for mounting to the head of a dental handpiece. U.S. Pat. No. 2,731,722 issued Wilen on Jan. 24, 1956, discloses a spoon-shaped tongue deflector and shield for attachment to a dental handpiece which has a tube for carrying a water spray. U.S. Pat. No. 2,924,013 issued to Wowra on Feb. 9, 1990; U.S. Pat. No. 1,516,933 issued to Terranova on Nov. 25, 1924; U.S. Pat. No. 1,152,122 issued to Samphere on Aug. 31, 1915; and U.S. Pat. No. 594,952 issued to Hoyer on Dec. 7, 1987, all disclose variously styled tongue and cheek shields for attachment to a dental handpiece.

In addition to the deficiencies previously described, none of these devices provides a viable solution to deflecting the tongue, aspirating liquids, and maintaining the mouth in an open position while, at the same time, maximizing the unencumbered work area for the dentist as well as providing control of the level of suction. Ideally, a single dental appliance would provide for deflecting the tongue, aspirating liquids with variable suction level, and maintaining the patient's mouth in an open position. None of the devices heretofore developed, however, meets the existing need for such a device. The present invention satisfies that need.

The foregoing patents reflect the state of the art of which the applicant is aware and are tendered with the view toward discharging applicant's acknowledged e duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

By way of example and not of limitation, the present invention generally comprises a tongue deflector in which a tubular channel extends longitudinally between its proximal end and a point near its distal end. An aspiration tube is slidably disposed in the channel, the distal end of the aspiration tube terminating near the distal end of the tongue deflector and the proximal end of the aspiration tube extending from the proximal end of the tongue deflector for attachment to a suction hose. A slot extending between the channel and the surface of the tongue deflector serves as an orifice into which liquids are drawn under suction. When the distal end of the aspiration tube is positioned against a wall at the distal end of the channel, suction is eliminated. By sliding the aspiration tube away from the distal end of the tongue deflector, the dentist can turn the suction on and control the level of suction within a range. As a result, liquids and fine particles are drawn into the aspiration tube through the space created between the end of the aspiration tube and the wall and the end of the channel.

Preferably an elongated bite "tube" is used to support the aspiration tube in a fixed position. The bite tube can be cylindrical-shaped, triangular-shaped, rectangular-shaped or the like. Preferably each end of the bite tube is open for insertion of a single upper and lower tooth, respectively, or, if a corresponding tooth is missing, the bite tube can be held in place by either a single upper or lower tooth and supported in the area of a missing tooth by a cotton roll. Therefore, an alternative embodiment could have one end open and the other end closed or otherwise configured for abutment against a cotton roll or the gums.

Preferably, the aspiration tube extends through the bite tube in a direction transverse to the longitudinal axis of the bite tube and is offset by a desired angle. Alternatively, the bite tube can be eliminated and the aspiration tube supported by a standoff bracket attached to a dental handpiece.

An object of the invention is to deflect the tongue to provide sufficient room in the lingual vestibule to perform any routine dental task.

Another object of the invention is to provide for suction of liquids without traumatizing soft tissue.

Another object of the invention is to deflect and shield the tongue from accidental injury from dental appliances.

Another object of the invention is to provide for aspiration of liquids with suction from the low level svedopter vacuum line, thereby freeing the high level vacuum line for other uses.

Another object of the invention is to comfortably maintain the patient's mouth in an open position.

Another object of the invention is to reduce the need for chairside assistance from a dental assistant, thereby freeing the dental assistant for other tasks.

Another object of the invention is to provide an aspirator and tongue deflector which can be stabilized with only one tooth.

Another object of the invention is to provide an aspirator and tongue deflector which is easy to install and remove, and which can be temporarily removed during a dental procedure.

Another object of the invention is to increase patient comfort during lengthy dental procedures.

Another object of the invention is to provide an aspirator and tongue deflector with a bite support tube which does not intrude into the area of the mouth being worked on.

Another object of the invention is to provide for control of the suction level, as well as to turn suction on and off without the need to use external controls.

Another object of the invention is to provide for performing dental procedures with greater speed and efficiency.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 is a perspective view of the apparatus of the present invention.

FIG. 8 is a diagrammatic perspective view of the apparatus of FIG. 1 depicting variable positioning of the bite tube in relation to the aspiration tube.

DESCRIPTION OF THE PREFERRED EMBODIMENTS

Referring more specifically to the drawings, for illustrative purposes the present invention is embodied in the apparatus generally shown in FIG. 1. It will be appreciated, however, that the apparatus may vary as to configuration and as to details of the parts without departing from the basic concepts as disclosed herein.

Figure 2:
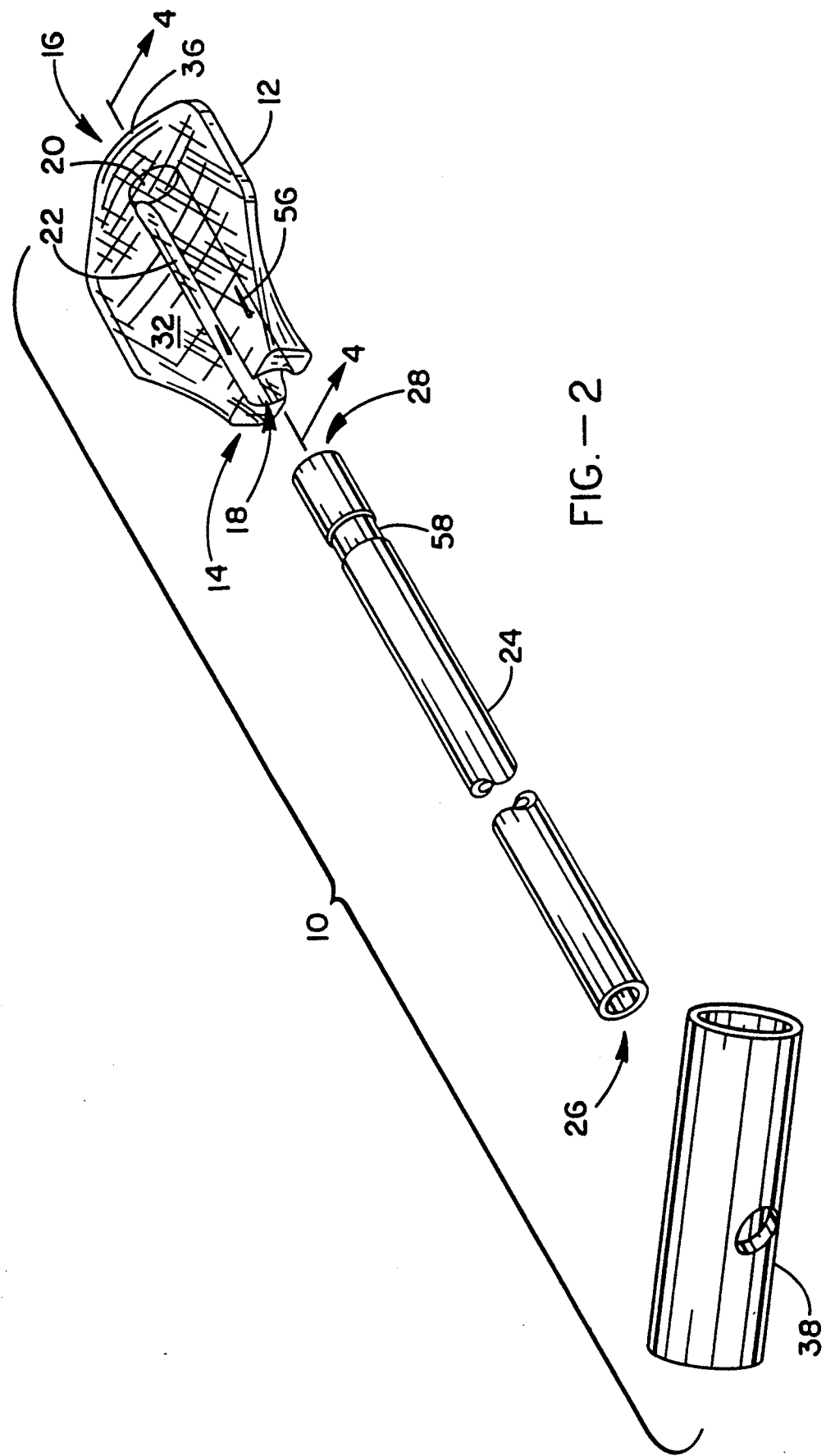
FIG. 2 is an exploded view of the apparatus shown in FIG. 1.

Referring to FIG. 1 and FIG. 2, the dental appliance 10 in accordance with the present invention includes a tongue deflector 12 having a proximal end 14 and a distal end 16. A generally tubular channel 18 extends from the proximal end 14 and terminates at a wall 20 near the distal end 16. A slot 22 runs the length of channel 18 and establishes an opening extending between channel 18 and the buccal surface 32 of tongue deflector 12. Preferably tongue deflector 12 is fabricated from plastic or the like, and is either disposable or suitable for sterilization after use. And, while other dimensions can be used, it is generally preferred that tongue deflector 12 be approximately one inch (2.54 cm) wide and approximately one inch (2.54 cm) in length.

An aspiration tube 24 having a proximal end 26 and a distal end 28 is slidably disposed in channel 18. Aspiration tube 24 is a generally cylindrical plastic or metal tube having an outer diameter which is slightly larger than the diameter of channel 18. By using a resilient material for tongue deflector 12, aspiration tube 24 can be inserted into channel 18 and moved toward or away from distal end 16 as desired. In this manner, tongue deflector 12 will frictionally engage aspiration tube 24 for a generally tight fit but yield sufficiently to permit aspiration tube 24 to be moved to various positions. Slot 22 spreads open so that channel 18 can receive aspiration tube 24 and then closes to permit such frictional engagement.

The distal end 28 of aspiration tube 24 is aligned with the distal end 16 of tongue deflector 12, whereas the proximal end 26 of aspiration tube 24 extends beyond the proximal end 14 of tongue deflector 12 leaving proximal end 26 free for coupling to a vacuum pump using a flexible hose or the like. By positioning the distal end 28 of aspiration tube 24 such that it is spaced apart from wall 20 in tongue deflector 12, a vacuum gap 30 is formed through which liquids and small particles can be aspirated. Sliding the distal 28 of aspiration tube 24 against wall 20 will turn off the suction, whereas sliding it away from wall 20 will turn on the suction. It should also be noted that tongue deflector 12 can be rotated 360 degrees about aspiration tube 24 so that its position in the mouth can be adjusted while maintaining a constant suction level. This feature also permits the device to be used on either side of the mouth with ease.

It is significant that sliding motion of aspiration tube 24 in relation to tongue deflector 12 controls the level of suction imparted by the apparatus. For example, variable suction is highly desirable when the apparatus is used on periodontal patients who have surgery and have exposed cementum on the root surface. The exposed cementum is an area which is highly sensitive to vacuum or air and, therefore, it is important to be able to reduce the suction to a comfortable level. Numerous other circumstances may arise where complete control of the suction level is required. It will be appreciated that, instead of aspiration tube 24 being slidably coupled to tongue deflector 18, aspiration tube 24 could be fixed in position. This configuration, however, would require use of multiple dental appliances 10 in order to provide for various levels of suction, or selection of a suction level which is generally acceptable for most patients.

Figure 3:
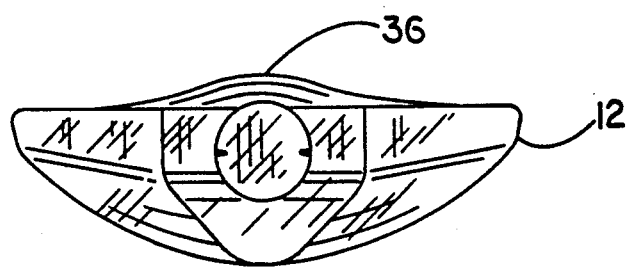
FIG. 3 is a view of the distal end of the tongue deflector portion of the apparatus shown in FIG. 1.
Figure 4:
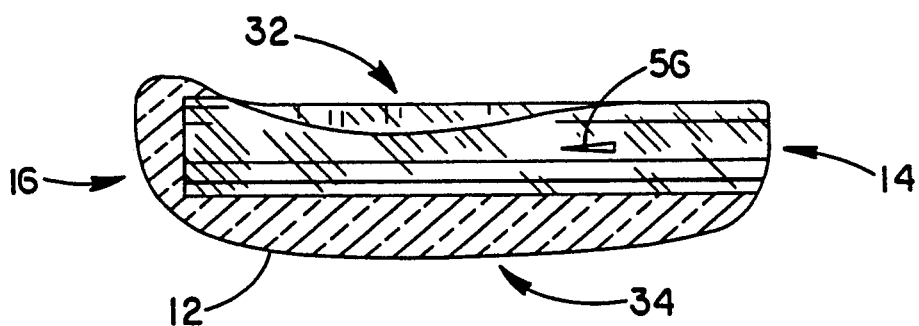
FIG. 4 is a cross-sectional view of the tongue deflector portion of the apparatus shown in FIG. 2 taken through line 4—4.

Referring now to FIG. 3 and FIG. 4, the buccal surface 32 of tongue deflector 12 has a generally concave curvature for a slight cup-like shape, whereas the lingual surface 34 of tongue deflector 12 has a complimentary generally convex curvature. The curvature on the buccal surface 32 allows fluids in the mouth to be directed toward vacuum gap 30 and removed. In addition, amalgam shavings can be placed directly into vacuum gap 30 and removed, thus decreasing any amounts of mercury which would otherwise be deposited in the mouth. The curvature of the lingual surface 34 gently holds the tongue away from the teeth and toward the mid area of the mouth, thereby limiting movement of the tongue and providing sufficient room for the dentist or hygienist to perform the required dental procedure.

A lobe 36 positioned at the distal end 28 projects above the buccal surface 32 of tongue deflector 12. Significantly, lobe 36 serves as a spacer to position vacuum gap 30 away from soft tissue in the mouth against which the buccal surface 32 and vacuum gap 30 would otherwise rest. This prevents soft tissue from being drawn into vacuum gap 30 and stopping the suction. At times, however, very soft sublingual tissue might be drawn into vacuum gap 30. In that event, any resulting blockage can be cleared by sliding aspiration tube 24 toward the proximal end 14 of tongue deflector 12 until vacuum gap 30 is open and suction is reestablished. Nevertheless, due to the low vacuum level employed no damage will result to the soft tissue that is drawn into vacuum gap 30.

Figures 5, 6, 7:
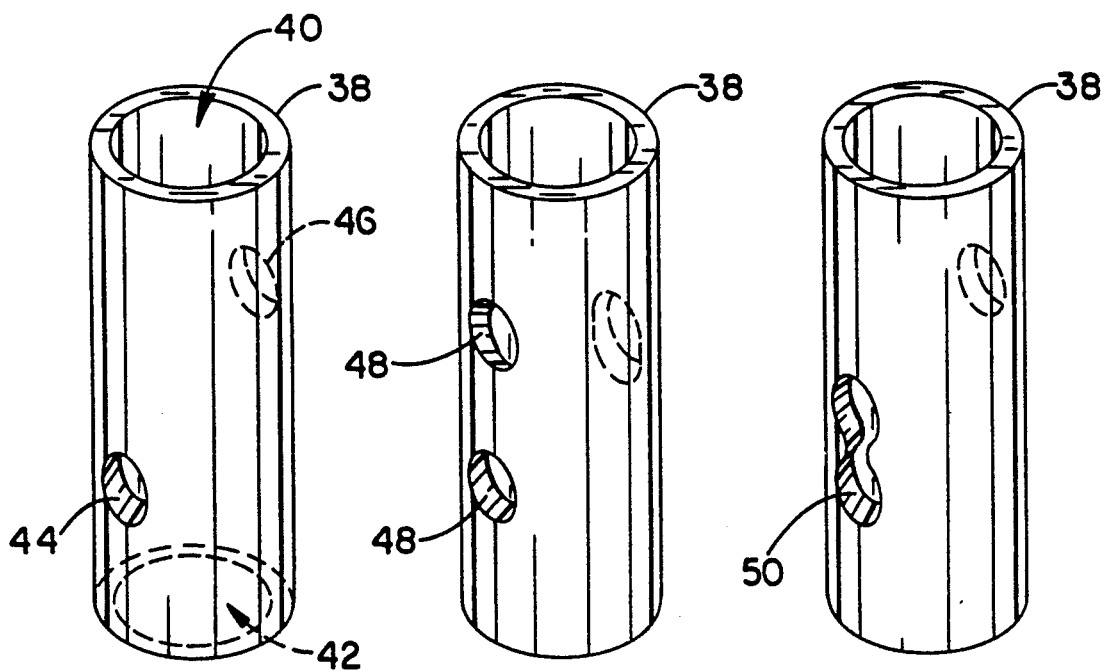
FIG. 5 is a perspective view of the bite tube portion of the apparatus shown in FIG. 1.
FIG. 6 is a first alternative embodiment of the bite tube shown in FIG. 5.
FIG. 7 is a second alternative embodiment of the bite tube shown in FIG. 5.

Referring now to FIG. 5, aspiration tube 24 is coupled to a bite tube 38 which supports and stabilizes tongue deflector 12. Preferably bite tube 38 is an elongated tubular member having an upper tooth receptacle 40 and a lower tooth receptacle 42. It will appreciated, however, that bite tube 38 can be cylindrical-shaped, triangular-shaped, rectangular-shaped or the like. It will also be appreciated that bite tube 38 could be hollow or, alternatively, it could be a solid member with hollowed ends to form upper tooth receptacle 40 and lower tooth receptacle 42. Bite tube 38 is preferably fabricated from a lightweight rigid material such as plastic or the like.

Aspiration tube 24 extends through anterior opening 44 and posterior opening 46 for support. Preferably, anterior opening 44 and posterior opening 46 are displaced by approximately 60 degrees as shown, so that aspiration tube 24 slants downward relative to a horizontal position. Alternatively, anterior opening 44 could be replaced with a plurality of openings 48 as shown in FIG. 6, or a contiguous slotted opening 50 as shown in FIG. 7 so that aspiration tube 24 could be adjusted to various angles. And, while an angle of 60 degrees is preferred, any angle within a range of approximately 45 degrees through 90 degrees could be employed.

The bite tube 38 is secured in the patient's mouth by having the patient gently bite down to insert opposing (one upper and one lower) teeth in upper receptacle 40 and lower receptacle 42, respectively. Alternatively, one tooth (either upper or lower) could be engaged in a receptacle and the other end of the bite tube supported by a cotton roll or the like between the bite tube and the gum tissue where an opposing tooth is missing. Note that the use of bite tube 38 is distinctly advantageous in that conventional bite blocks must be secured in place with several upper and lower teeth. The present invention, however, can be secured in place even though a patient is missing teeth.

In general, bite tube 38 is secured on the side of the mouth opposite from the side of the mouth on which the dental procedure will be performed so that the tongue is retracted away from the work area. Referring also to FIG. 8, it can be seen that different sizes of the mouth, as well as work area positions, can be accommodated by sliding aspiration tube 24 back and forth in bite tube 38 until tongue deflector 12 is in the desired position.

Figure 9:
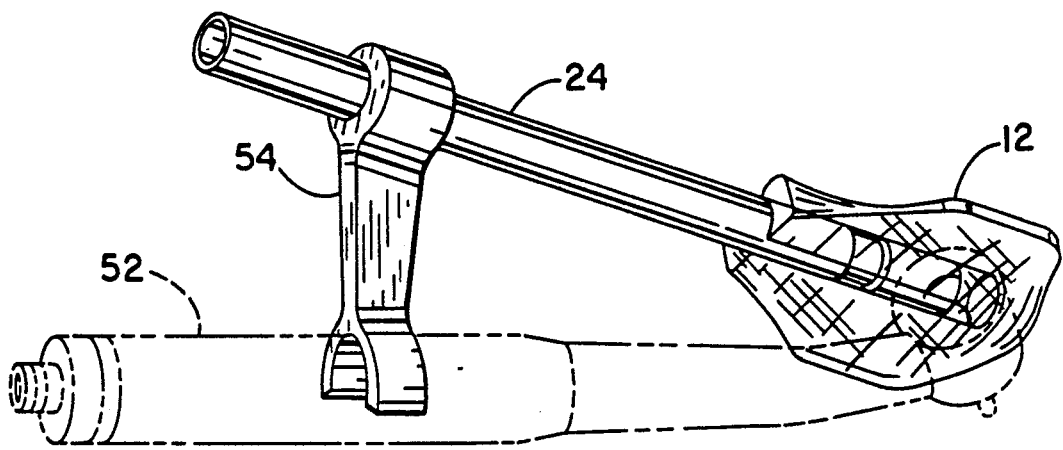
FIG. 9 shows an alternative embodiment of the invention.

FIG. 9 shows an alternative embodiment of the invention. While it is preferred to support aspiration tube 24 and tongue deflector 12 with a bite tube 38, there may be occasions where it is desirable to dispense with the bite tube and to use a conventional dental handpiece 52 for support. In this configuration, a standoff bracket 54 or the like would be used to couple aspiration tube 24 to the handpiece 52. Aspiration tube 24 would extend though one end of standoff bracket 54 while the other end of standoff bracket 54 would be coupled to dental handpiece 52. By doing so, the dentist or hygienist can reposition tongue deflector 12 (and vacuum gap 30) as handpiece 52 is moved.

Referring again to FIG. 1 and FIG. 2, to prevent aspiration tube 24 from being completely withdrawn from channel 18 and thereby separated from tongue deflector 12, at least one (and preferably a plurality) of barbs 56 extend at and angle from the inner surface of channel 18 toward distal end 16 of tongue deflector 12. When aspiration tube 24 is withdrawn, barbs 56 will engage an annular groove or notch 58 in the tube, thereby preventing aspiration tube 24 from being removed from tongue deflector 12. Placement of barbs 56 and notch 58 is such that aspiration tube 24 can slide toward and away from distal end 16 to control the level of suction, notwithstanding prevention of removal. Upon insertion of aspiration tube 24, however, barbs 56 will deflect such that they do not engage notch 58.

Accordingly, it will be seen that this invention provides for stabilization of the patient's mouth in an open position as well as deflecting the tongue while removing liquid which would otherwise accumulate in the mouth. Therefore, difficult dental procedures can be performed with minimal discomfort to the patient and with less distraction to the dentist which would otherwise occur where multiple dental appliances are required to serve the same function. For example, lower molar crown preparations or fillings on the opposite side of the mouth generally require retraction of the tongue by the dentist and use of a mouth mirror while trying to work on the lingual side of the tooth and trying to keep the area from filling up with saliva and debris. The present invention will serve to retract the tongue and keep the work area free of liquid at the same time, as well as to reduce back strain to the dentist or hygienist who would otherwise be using several dental appliances to accomplish the same task as the present invention. As a result, the dentist and hygienist can work more efficiently, thereby reducing the cost of the procedure. At the same time, the patient is made more comfortable while undergoing treatment.

Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. A dental appliance for deflecting the tongue and aspirating liquids in the mouth of a patient undergoing dental work, comprising:
   (a) tongue deflector means for limiting movement of the tongue,
   (b) suction means, slidably coupled to said tongue deflector means, for aspirating liquids in the mouth and controlling the level of suction by sliding motion in relation to said tongue deflector means;
   (c) spacer means for maintaining sufficient space between said suction means and soft tissue in the mouth so as to minimize said soft tissue being drawn into said suction means, said spacer means joined to and extending from said tongue deflector means; and
   (d) support means for securing said tongue deflector means and said suction means in the mouth, said support means slidably coupled to said suction means, said support means having an open first end and an open second end, said first and second ends forming first and second tooth receptacles, whereby said support means is secured in the mouth by placing a tooth in at least one of said tooth receptacles and biting down on said support means.

2. An apparatus as recited in claim 1, said tongue deflector means including a proximal end, a distal end, a first surface and a second surface, said tongue deflector means including a tubular channel extending from said proximal end and terminating near said distal end, said tongue deflector means including a slot extending from said tubular channel to said first surface.

3. An apparatus as recited in claim 2, wherein said suction means comprises a tube, said tube having a proximal end and a distal end, said distal end of said tube aligned with said distal end of said tongue deflector means.

4. An apparatus as recited in claim 3, wherein said spacer means comprises a lobe disposed at said distal end and extending from said first surface of said tongue deflector means.

5. An apparatus as recited in claim 4, wherein said first surface of said tongue deflector means has a generally concave curvature.

6. An apparatus as recited in claim 3, further comprising at least one barb, said barb extending from said tubular channel toward said distal end of said tongue deflector means, said tube including an annular notch for engagement of said barb, whereby said tube deflects said barb upon insertion of said tube into said channel and said notch engages said barb to prevent removal of said tube.

7. An apparatus for aspirating liquids and positioning the tongue during dental procedures, comprising:
   (a) a tongue deflector having a proximal end, a distal end, a first surface and a second surface, said tongue deflector including a tubular channel extending from said proximal end and terminating near said distal end, said tongue deflector including a slot extending from said tubular channel to said first surface;
   (b) a suction tube slidably coupled to said tongue deflector, said suction tube having a proximal end and a distal end, said distal end of said suction tube aligned with said distal end of said tongue deflector, whereby sliding said suction tube in relation to said tongue deflector controls the level of suction;
   (c) a lobe disposed at said distal end and extending from said first surface of said tongue deflector; and
   (d) support means for securing said tongue deflector and said suction tube in the mouth, said support means slidably coupled to said suction tube, said support means having an open first end and an open second end, said first and second ends forming first and second tooth receptacles, whereby said support means is secured in the mouth by placing a tooth in at least one of said tooth receptacles and biting down on said support means.

8. An apparatus as recited in claim 7, wherein said first surface of said tongue deflector has a generally concave curvature.

9. An apparatus as recited in claim 8, further comprising at least one barb, said barb extending from said tubular channel toward said distal end of said tongue deflector, said tube including an annular notch for engagement of said barb, whereby said tube deflects said barb upon insertion of said tube into said channel and said notch engages said barb to prevent removal of said tube.

10. An apparatus for deflecting the tongue, removing liquid from the mouth, and maintaining the mouth in an open position during dental procedures, comprising:
    (a) a tongue deflector, said tongue deflector having a proximal end and a distal end, a concave first surface and a convex second surface, a tubular channel extending from said proximal end and terminating near said distal end, and a slot extending from said channel to said first surface;
    (b) an aspiration tube, said aspiration tube slidably disposed within said channel, said aspiration tube having a proximal end and a distal end, said distal end of said tube aligned with said distal end of said tongue deflector;
    (c) said tongue deflector including a lobe, said lobe disposed at said distal end and extending from said first surface of said tongue deflector; and
    (d) a bite tube, said bite tube having an open first end and an open second end, said first and second ends forming first and second tooth receptacles, whereby said bite tube is secured in the mouth by placing a tooth in at least one of said tooth receptacles and biting down on said bite tube, said bite tube having an anterior opening and a posterior opening, said aspiration tube extending through said anterior opening and said posterior opening.

11. An apparatus as recited in claim 10, wherein said bite tube is slidably moveable along said aspiration tube.

12. An apparatus as recited in claim 11, further comprising at least one barb, said barb extending from said tubular channel toward said distal end of said tongue deflector, said tube including an annular notch for engagement of said barb, whereby said tube deflects said barb upon insertion of said tube into said channel and said notch engages said barb to prevent removal of said tube.

13. An apparatus for aspiration and tongue deflection during dental procedures in the mouth of a patient, comprising:
(a) tongue deflector means for limiting movement of the tongue;
(b) suction means for aspirating liquids in the mouth, said suction means coupled to said tongue deflector means;
(c) spacer means for maintaining sufficient space between said suction means and soft tissue in the mouth so as to minimize said soft tissue being drawn into said suction means, said spacer means joined to and extending from said tongue deflector means; and
(d) support means for securing said tongue deflector means and said suction means in the mouth, said support means slidably coupled to said suction means, said support means having an open first end and an open second end, said first and second ends forming first and second tooth receptacles, whereby said support means is secured in the mouth by placing a tooth in at least one of said tooth receptacles and biting down on said support means.

14. An apparatus as recited in claim 13, wherein said tongue deflector means includes a proximal end, a distal end, a first surface and a second surface and wherein said suction means comprises a tube, said tube having a proximal end and a distal end, said distal end of said tube generally aligned with said distal end of said tongue deflector means.

15. An apparatus as recited in claim 14, wherein said spacer means comprises a lobe disposed at said distal end and extending from said first surface of said tongue deflector means.

16. An apparatus as recited in claim 15, wherein said first surface of said tongue deflector means has a generally concave curvature.

17. A dental appliance for deflecting the tongue and aspirating liquids in the mouth of a patient undergoing dental work, comprising:
(a) tongue deflector means for limiting movement of the tongue, said tongue deflector means including a proximal end, a distal end, a first surface and a second surface, said first surface having a generally concave curvature, said tongue deflector means including a tubular channel extending from said proximal end and terminating near said distal end, said tongue deflector means including a slot extending from said tubular channel to said first surface;
(b) a tube slidably coupled to said tongue deflector means, said tube having a proximal end and a distal end, said distal end of said tube aligned with said distal end of said tongue deflector means;
(c) a lobe disposed at said distal end and extending from said first surface of said tongue deflector means;
(d) support means for securing said tongue deflector means and said suction means in the mouth, said support means slidably coupled to said suction means; and
(e) at least one barb, said barb extending from said tubular channel toward said distal end of said tongue deflector means, said tube including an annular notch for engagement of said barb, whereby said tube deflects said barb upon insertion of said tube into said channel and said notch engages said barb to prevent removal of said tube.

18. An apparatus for aspirating liquids and positioning the tongue during dental procedures, comprising:
(a) a tongue deflector having a proximal end, a distal end, a first surface and a second surface, said first surface having a generally concave curvature, said tongue deflector including a tubular channel extending from said proximal end and terminating near said distal end, said tongue deflector including a slot extending from said tubular channel to said first surface;
(b) a suction tube slidably coupled to said tongue deflector, said suction tube having a proximal end and a distal end, said distal end of said suction tube aligned with said distal end of said tongue deflector, whereby sliding said suction tube in relation to said tongue deflector controls the level of suction;
(c) a lobe disposed at said distal end and extending from said first surface of said tongue deflector; and
(d) support means for securing said tongue deflector and said suction tube in the mouth, said support means slidably coupled to said suction tube; and
(e) at least one barb, said barb extending from said tubular channel toward said distal end of said tongue deflector, said suction tube including an annular notch for engagement of said barb, whereby said suction tube deflects said barb upon insertion of said suction tube into said channel and said notch engages said barb to prevent removal of said suction tube.

19. An apparatus for deflecting the tongue, removing liquid from the mouth, and maintaining the mouth in an open position during dental procedures, comprising:
(a) a tongue deflector, said tongue deflector having a proximal end and a distal end, a concave first surface and a convex second surface, a tubular channel extending from said proximal end and terminating near said distal end, and a slot extending from said channel to said first surface;
(b) an aspiration tube, said aspiration tube slidably disposed within said channel, said aspiration tube having a proximal end and a distal end, said distal end of said tube aligned with said distal end of said tongue deflector;
(c) said tongue deflector including a lobe, said lobe disposed at said distal end and extending from said first surface of said tongue deflector;
(d) a bite tube, said bite tube having a first tooth receptacle and a second tooth receptacle, said bite tube having an anterior opening and a posterior opening, said aspiration tube extending through said anterior opening and said posterior opening, said bite tube slidably coupled to said aspiration tube; and
(e) at least one barb, said barb extending from said tubular channel toward said distal end of said tongue deflector, said aspiration tube including an annular notch for engagement of said barb, whereby said aspiration tube deflects said barb upon insertion of said aspiration tube into said channel and said notch engages said barb to prevent removal of said aspiration tube.

* * * * *